United States Patent [19]
Borror
[11] 4,028,353
[45] June 7, 1977

[54] NOVEL CHEMICAL COMPOUNDS

[75] Inventor: Alan L. Borror, Lexington, Mass.
[73] Assignee: Polaroid Corporation, Cambridge, Mass.

[22] Filed: Nov. 30, 1972
[21] Appl. No.: 310,942

Related U.S. Application Data

[63] Continuation of Ser. No. 167,500, July 29, 1971, Pat. No. 3,734,739.

[52] U.S. Cl. .......................... 260/240.6; 260/240.4; 260/240.65; 260/240.7
[51] Int. Cl.[2] ........................................ C07D 403/06
[58] Field of Search ....... 260/240.6, 240.65, 240.7, 260/240.4

[56] References Cited

UNITED STATES PATENTS

| | | | |
|---|---|---|---|
| 2,231,658 | 2/1941 | Brooker et al. | 95/7 |
| 2,256,163 | 9/1941 | Kumetat et al. | 95/7 |
| 2,503,776 | 4/1950 | Sprague | 260/240.5 |

OTHER PUBLICATIONS

Hamer, The Cyanine Dyes & Related Compounds, (Interscience, N.Y., 1964), pp. 297–300.
Venkataraman, The Chemistry of Synthetic Dyes, (American Press, N.Y., 1971), pp. 249–252.

*Primary Examiner*—Cecilia M. S. Jaisle
*Attorney, Agent, or Firm*—Philip G. Kiely; Robert M. Ford; Mart C. Matthews

[57] ABSTRACT

The present invention relates to photography and, more particularly, to a novel spectrally (optically) sensitized radiation recording photographic element which comprises a cyanine dye of the formula:

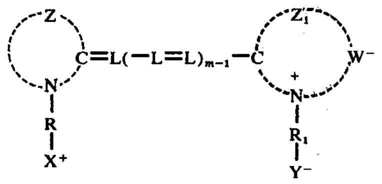

wherein L represents a methine group; *m* represents a positive integer of from 1 to 3, inclusive; Z and $Z_1$ each represents the nonmetallic atoms necessary to complete a cyanine dye heterocyclic ring system containing a 5 or 6 membered heterocyclic nucleus; R and $R_1$ each represents a divalent acyclic or cyclic group; $X^+$ represents a quaternary ammonium, sulfonium or phosphonium group; $Y^-$ represents a $-SO_3^-$ or $-COO^-$ group; and $W^-$ represents an anion.

8 Claims, No Drawings

NOVEL CHEMICAL COMPOUNDS

CROSS REFERENCE TO RELATED APPLICATIONS

This application is in part a continuation of my copending U.S. patent application Ser. No. 167,500, filed July 29, 1971, now U.S. Pat. No. 3,734,739.

BACKGROUND OF THE INVENTION

1. Field of the invention

The present invention is directed to providing novel spectrally (optically) sensitized radiation recording photographic elements.

2. Description of the prior art

In accordance with techniques disclosed in the prior art, photosensitive elements and particularly photosensitive silver halide elements may be provided with increased electromagnetic radiation absorption and photchemical reponse by specified sensitization procedures.

Among such procedures is found a technique categorized, and denoted, as chemical sensitization, wherein a photosensitive element, and particularly a photosensitive silver halide element, may be treated with compounds such as various sulfur compounds, for example, those set forth in U.S. Pat. Nos. 1,574,944; 1,623,499 and 2,410,689; salts of noble metals such as ruthenium, rhodium, palladium, iridium and platinum, all of which belong to Group III of the Periodic Table of Elements and have an atomic weight greater than 100, for example, potassium chloroplatinate, sodium chloropalladite, ammonium chlororhodinate, and the like, in amounts below that which produces any substantial fog inhibition, as described in U.S. Pat. No. 2,488,060; gold salts, for example, potassium aurothiocyanate, potassium chloroaurate, auric trichloride, and the like, as described in U.S. Pat. Nos. 2,597,856 and 2,597,915; reducing agents such as stannous salts, for example, stannous chloride, as described in U.S. Pat. No. 2,487,850, individually or in combination. Such chemical sensitization procedures provide increased response to electromagnetic radiation by the photoresponsive silver halide treated over the frequency range of the inherent, or natural, response characteristics of the crystal.

A second procedure comprises a technique categorized, and denoted, as a spectral, or optical, sensitization procedure, wherein a photosensitive material, and particularly photosensitive silver halide, is provided frequency-selective electromagnetic radiation reponse characteristics and/or an increase in its inherent, or natural, spectral response characteristics.

In general, such spectral sensitization procedures are accomplished by the adsorption onto one or more surfaces of the photosensitive material of one or more dyes selected from certain classes of dyes including, preferably, cyanine dyes and dyes related to them. For an extensive treatment of cyanine dyes particularly adapted to provide spectral sensitization of, for example, a photosensitive silver halide crystal see Hamer, F. M., *The Cyanine Dyes and Related Compounds*, Interscience Publishers, New York, N.Y., U.S.A., (1964).

By means of the traditional procedures disclosed in the art as adapted to accomplish spectral sensitization of photosensitive material, and preferably sensitization of photosensitive silver halide, a cyanine dye in the form of polymeric aggregates is adsorbed to the receptive faces, or surfaces, of the photoresponsive material in a statistical monomolecular layer thickness or less. Generally, the cyanine dyes preferably employed for purposes of spectral sensitization comprise an amidinium ion system in which both of the nitrogen atoms are included within separate heterocyclic ring systems, and in which the conjugated chain joining the nitrogen atoms passes through a portion of each heterocyclic ring merocyanine. Adsorption is generally believed to be partly accomplished by an unknown type of chemiadsorption between negative crystal surface charges provided, for example, by the excess halide components of the silver halide, and the positive charge of the cyanine chromophore. Adsorption is also favored by the ability to form silver complexes with nuclei containing an amidinium nitrogen atom of a selected cyanine dye's heterocyclic ring system, or systems, for example, with a nuclear sulfur, oxygen, or selenium atom, or a second nuclear nitrogen atom not directly a component of the amidinium ion system.

It has also been understood that the efficiency of the spectral sensitization of a, for example, silver halide crystal increases in accordance with an increase in the chemiadsorption of the selected sensitizing dye, in the form of polymeric aggregates, on the appropriate surfaces, or faces, of the crystal up to the concentration at which increase of sensitivity peaks or plateaus. Specifically, maximum sensitization has been found ordinarily to occur at a dye concentration level less than or equal to a statistical monomolecular layer of dye coverage on the adsorbing surfaces of the crystal, usually just short of monomolecular coverage of the crystal surface.

Sensitivity conferred by a sensitizing dye thus does not increase proportionately to the concentration of the dye, but rather passes through a maximum as concentration is increased. Attempts to increase the spectral sensitivity of the crystal by increasing the concentration of sensitizing dye adsorbed by its appropriate surfaces beyond the plateau or peak concentration level, provide a progressive decrease in spectral sensitivity as the concentration is so increased; see: Hamer, F. M., *The Cyanine Dyes and Related Compounds*, supra, and Borin, A. V., *Investigation of the Concentration Effect in Optical Sensitization of Photographic Emulsions*, Uspekhi Nauch. Fab. Akad. Nauk. SSSR, Otdel. Ihim. Nauk. 7, 183–190 (1960). In many instances, this resultant decrease in the crystal's spectral sensitivity attains catastrophic proportions when the relative amount of dye necessary to provide a given incremental increase in sensitivity, prior to attainment of the plateau or peak region, is compared with the same amount of dye, in excess of that which provides optimum sensitization.

The energy or charge-carrier absorptive propensity of a photoresponsive element comprising a particulate dispersion of photosensitive material is generally dependent upon the effective, adsorbed presence of sufficient dye to effect maximum absorption of, and transfer of, electromagnetic energy-induced photoreaction stimulus to the photosensitive material. The aforementioned monomolecular layer adsorption of the dye to the appropriate surfaces of the photosensitive material fails, by a relatively large degree, to provide complete absorption of incident radiation. In fact, in conventional optically sensitized, photographic, photoresponsive elements, such as panchromatic photographic emulsions, coated on a suitable supporting member, comprising a relatively thin layer, for example, on the order of about 7 microns in thickness, and including a dispersion of photoresponsive silver halide in a gelatin matrix, for example, in a concentration of about 100 mgs. of silver per square foot, the photoresponsive element only absorbs roughly in the order of less than one-third of the available incident light, over the radiation frequency range desired for photographic employment of the element, with the concomitant failure of such elements to even approximate their potential, or theoretical, efficiency. The maximum absorbed radiation attributable to a given monomolecular dye layer adsorbed on a photosensitive crystal is about 7 percent of the total incident radiation. W. West and V. I. Saunders, *Wissenschaftliche Photographie*, W. Eichler, H. Frieser and O. Helwich, eds., Verlag Dr. O. Helwich, Darmstadt, 1958, p. 48. The net response of the system thus cannot be improved by simply adding more of the same sensitizing dye, but must be achieved by development of more efficient and effective sensitizing dye systems.

In U.S. Pat. Nos. 2,213,995 and 2,231,658 there is disclosed cyanine dyes wherein $X^+$ of Formula I, infra, is a —COOH group and $Y^-$ is a $—COO^-$ group; U.S. Pat. Nos. 2,503,776; 2,519,001; and 2,912,329, and British Pat. No. 742,112, German Pat. No. 929,080, Belgian Pat. No. 532,409 disclose cyanine dyes wherein $X^+$ of Formula I is a $—SO_3H$ group and $Y^-$ is a $—S\,0_3^-$ group; German Pat. No. 1,028,718 discloses cyanine dyes wherein $X^+$ of Formula I is an alkyl group and $Y^-$ is a $—O—SO_3^-$ group; German Pat. No. 1,916,845 discloses cyanine dyes wherein $X^+$ of Formula I is a $—S—SO_3H$ group; and $Y^-$ is a $—S—SO_3^-$ group; and U.S. Pat. Nos. 2,256,163 and 2,354,524 disclose cyanine dyes wherein $X^+$ of Formula I is a $—^+N(alkyl)_3$ group and $Y^-$ is an alkyl group.

SUMMARY OF THE INVENTION

The present invention is directed to a novel spectrally (optically) sensitized radiation recording photographic element which comprises a cyanine dye of the formula:

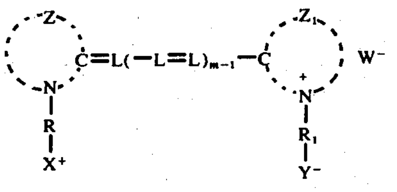

wherein L represents a methine group; *m* represents a positive integer of from 1 to 3, inclusive; Z and $Z_1$ each represents the nonmetallic atoms necessary to complete a cyanine dye heterocyclic ring system containing a 5 or 6 membered heterocyclic nucleus; R and $R_1$ each represents a divalent acylic or cyclic group; $X^+$ represents a quaternary ammonium, sulfonium or phosphonium group; $Y^-$ represents a $—SO_3^-$ or a $—COO^-$ group; and $W^-$ represents an anion.

DETAILED DESCRIPTION OF THE INVENTION

As previously characterized, the present invention is directed to a novel spectrally (optically) sensitized radiation recording photographic element comprising a cyanine dye of Formula I, supra.

As examples of heterocyclic ring systems containing a 5 or 6 membered heterocyclic nucleus contemplated for employment in the practice of the present invention, mention may be made of the traditional art-recognized heterocyclic ring systems customarily employed as constituent components of cyanine dyes such as heterocyclic ring systems of the azole series including those of the thiadiazole and thiazole series, for example, thiazole; 4-methylthiazole; 4-phenylthiazole; 5-methylthiazole; 5-phenylthiazole; 4,5-dimethylthiazole; 4,5diphenylthiazole; 4-(2-thienyl)-thiazole; etc.; of the benzothiazole series, for example, benzothiazole; 4-chloro-benzothiazole; 5-chloro-benzothiazole; 6-chloro-benzothiazole; 7-chloro-benzothiazole; 4-methyl-benzothiazole; 5-methyl-benzothiazole; 6-methyl-benzothiazole; 6-bromobenzothiazole; 4-phenyl-benzothiazole; 5-phenyl-benzothiazole; 4-methoxy-benzothiazole; 5-methoxy-benzothiazole; 6-methoxybenzothiazole; 5-iodo-benzothiazole; 6-iodo-benzothiazole; 5-ethoxy-benzothiazole; 6-ethoxy-benzothiazole; 5,6-dimethoxy-benzothiazole; 5-hydroxy-benzothiazole; 6-hydroxy-benzothiazole; 5-bromo-benzothiazole; 4-ethoxy-benzothiazole; tetrahydrobenzothiazole; 5,6-dioxymethylene-benzothiazole; etc.; and of the naphthothiazole series, for example, α-naphthothiazole; β-naphthothiazole; β,β-anphthothiazole; 5-methoxy-β-naphthothiazole; 5-ethoxy-β-naphthothiazole; 7-methoxy-β-naphthothiazole; 8-methoxy-α-naphthothiazole; etc.; those of the selenazole series, for example, 4-methylselenazole; 4-phenylselenazole; etc., including those of the benzoselenazole series, for example, benzoselenazole; 5-chloro-benzoselenazole; 5-methoxy-benzoselenazole; 5-hydroxy-benzoselenazole; tetrahydrobenzoselenazole; etc.; and of the naphthoselenazole series, for example, β-naphthoselenazole; α-naphthoselenazole; etc.; those of the oxadiazole and oxazole series, for example, 5,methyloxazole; 4-phenyloxazole; 4,5-diphenyloxazole; 4-methyloxazole; 5-phenyloxazole; 4,5-dimethyloxazole; etc., including those of the benzoxazole series, for example, benzoxazole; 5-methylbenzoxazole; 6-methylbenzoxazole; 5,6-dimethylbenzoxazole; 5-methoxybenzoxazole; 5-phenylbenzoxazole; 5-carboxybenzoxazole; 5-sulfobenzoxazole; 5-chloro-benzoxazole; 5-sulfomylbenzoxazole; 6-dialkyl-amino-benzoxazole; 5-ethoxybenzoxazole; 6-methoxybenzoxazole; etc.; and of the naphthoxazole series, for example, 4,5-benzobenzoxazole; 5,6-benzobenzoxazole; 6,7-benzobenzoxazole; etc.; and those of the imidazole series, for example, 1-ethylimidazole; 1-ethyl-4-phenylimidazole; 1-ethyl-4,5-dimethylimidazole; etc.; of the benzimidazole series, for example, 5-chloro-benzimidazole; 5,6-dichlorobenzimidazole; 5-trifluoromethyl-benzimidazole; 5-cyanobenzimidazole; 5-carboxybenzimidazole; 5,6-dimethylbenzimidazole; etc.; and of the azine series including those of the pyridine series such as of the 2-pyridine series, for example, pyridine; 3-methylpyridine; 4-methylpyridine; 5-methylpyridine; 3,4-dimethylpyridine; 3,5-dimethylpyridine; 3,6-dimethyl-2-pyridine; 4,5-dimethyl-2-pyridine; 4-chloro-2-pyridine; 5-chloro-2-pyridine; 6-chloro-2-pyridine; 3-hydroxy-2-pyridine; 4-hydroxy-2-pyridine; 5-hydroxy-2-pyridine; 2-phenyl-2-pyridine; 6-phenyl-2-pyridine; etc.; of the 4-pyridine series, for example, 2-methyl-4-pyridine; 3-methyl-4-pyridine; 2-chloro-4-pyridine; 3-chloro-4-pyridine; 2,3-dimethyl-4-pyridine; 2-hydroxy-4-pyridine; 3-hydroxy-4-pyridine; etc.; of the pyrroline series; of the piperidine series; of the pyrimidine series; of the triazine series; of the thiazine series; of the thiazoline series, for example, thiazoline; 4-methyl-thiazoline; etc.; of the indolenine series such as of the 3,3-dialkylindoline series, for example, 3,3-dimethylindolenine; etc.; and of the quinoline series such as of the 2-quinoline series, for example, 2-quinoline; 3-methyl-2-quinoline; 5-methyl-2-quinoline; 7-methyl-2-quinoline; 6-chloro-2-quinoline; 8-chloro-2-quinoline; 6-methoxy-2-quinoline; 6-ethoxy-2-quinoline; 6-hydroxy-3quinoline; 8-hydroxy-2-quinoline; etc.; and of the 4-quinoline series, for example, 4-quinoline; 6-methoxy-4-quinoline; 6-methoxy-4-quinoline; 7-methyl-4-quinoline; 8-methyl-4-quinoline; etc.

As will be recognized from the foregoing the heterocyclic nuclei set forth may readily comprise the various substituents known in the cyanine dye art as, for example, alkyl, halogen, alkoxy, hydroxy, aralkyl, aryl, acyl, amino, carboxamido, carbamyl, sulfonamido, sulfamyl, thio, cyano, heterocyclic, etc., substituents.

As examples of the anions, represented by the term "$W^-$" in the formulae set forth herein, contemplated for employment in the practice of the present invention mention may be made of the anionic acid anion radicals customarily employed in the cyanine dye art, such as, for example, $Cl^-$, $Br^-$, $I^-$, $ClO_4^-$, $HSO_4^-$, $SO_3CH_3^-$, $SO_3C_2H_5^-$, $SO_3C_6H_5$, $SO_3C_6H_4CH_3^-$, acetate, propionate, cyanate, etc.

As examples of the quaternary ammonium, sulfonium and phosphonium groups, represented by the term"$X^+$" in the formulae set forth herein, contemplated for employment in the practice of the present invention mention may be made of

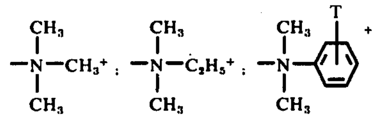

wherein T is hydrogen, lower alkyl, lower alkoxy, halogen, etc.;

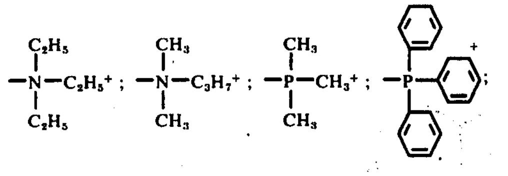

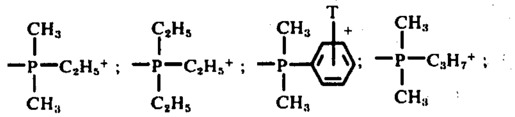

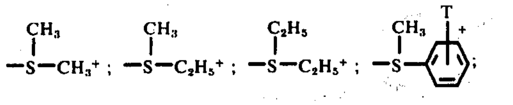

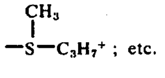

As examples of the divalent acyclic and cyclic groups, represented by the terms R and $R_1$ in the formulae set forth herein, contemplated for employment in the practice of the present invention mention may be made of an alkylene or olefinically unsaturated straight or branched chain divalent aliphatic group preferably comprising up to 5 carbon atoms such as, for example, methylene, ethylene, propylene, isopropylene, butylene, isobutylene, allylene, etc., which may include substituents such as, for example, halogen atoms such as chloride, hydroxyl, alkoxy, etc.; a cycloalkylene group such as, for example, a divalent cyclohexylene group; a divalent aryl group such as, for example, a divalent phenyl group —$\phi$—$CH_2$, —$\phi$—$CH_2CH_2$—, etc; a straight or branched chain aliphatic group possessing at least one chain carbon atom replaced by a hetero atom such as —S—, —O—, etc., for example, —$R_9$—O—, —$R_9$—S—, —$R_9$—O—$R_9$—, —$R_9$—S—$R_9$—, and the like wherein $R_9$ preferably constitutes an alkylene radical comprising from 1 to 4 carbon atoms and which may possess the aforementioned substituents.

Preferred cyanine dyes within Formula I for employment in the practice of the present invention comprise a dye of the formula:

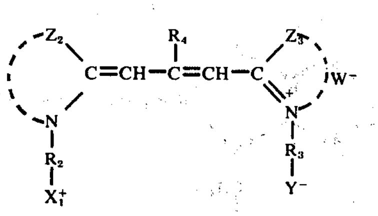

II wherein $Z_2$ and $Z_3$ each represents the nonmetallic atoms necessary to complete a heterocyclic ring system containing a thiazole, selenazole, oxazole, imidazole or pyridine nucleus; $R_2$ and $R_3$ each represents a divalent aliphatic group comprising from 1 to 5 carbon atoms; $R_4$ represents an alkyl group comprising from 1 to 5 carbon atoms or an aromatic group comprising 6 nuclear carbon atoms; $X^+$ represents a —$N^+(R_5)_3$ group wherein each $R_5$ represents an alkyl group comprising from 1 to 4 carbon atoms; $Y^-$ represents a —$SO_3^-$ or a —$COO^-$ group; and $W^-$ represents an anion and particularly preferred dyes comprise those within the formula:

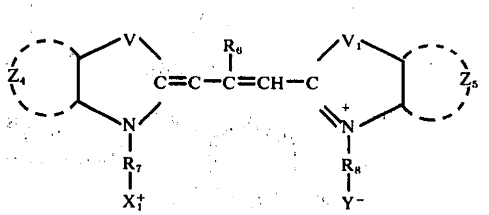

III wherein V and $V_1$ each represents oxygen, selenium, sulfur or

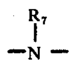

wherein $R_{13}$ represents an alkyl group comprising from 1 to 5 carbon atoms; $Z_4$ and $Z_5$ each comprises the nonmetallic atoms necessary to complete and annulated benzene or naphthalene; $R_6$ represents a hydrogen, methyl or ethyl group; $W^-$ represents an anion; $R_7$ and $R_8$ each represents an alkylene group comprising from 1 to 5 carbon atoms; $X^+$ represents a —$N^+(R_5)_3$ wherein each $R_5$ represents an alkyl group comprising from 1 to 4 carbon atoms; and $Y^-$ represents a —$SO_3^-$ or a —$COO^-$ group.

As examples of cyanine dyes within Formula I mention may be made of:

(A)
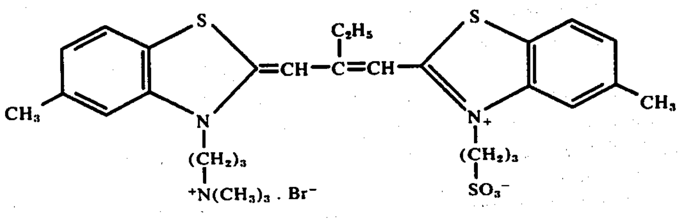
(B)
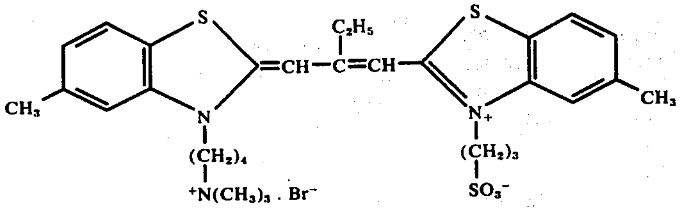
(C)
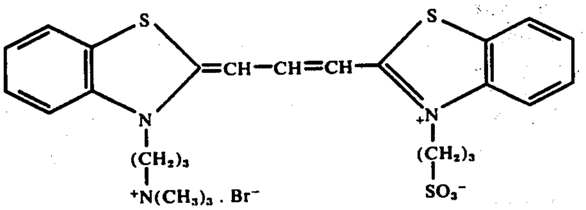
(D)
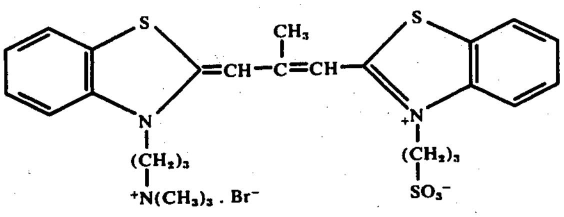
(E)
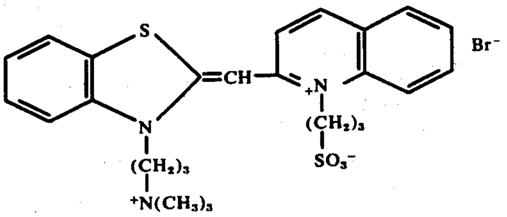
(F)
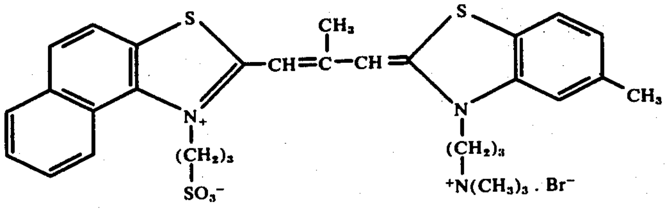
(G)
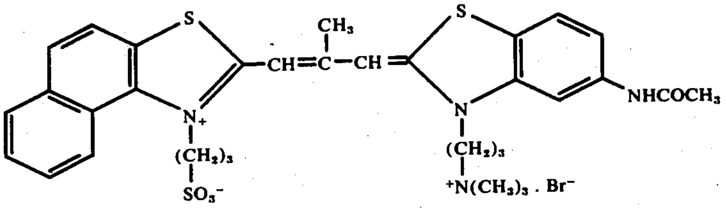
(H)
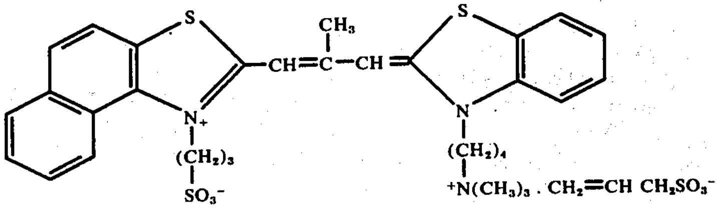

-continued
(I)
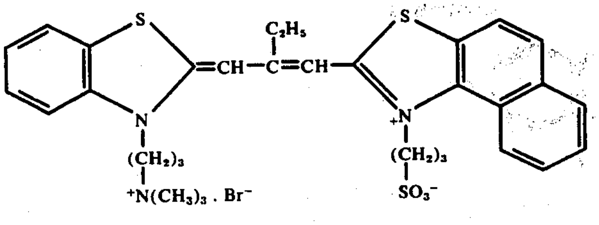
(J)
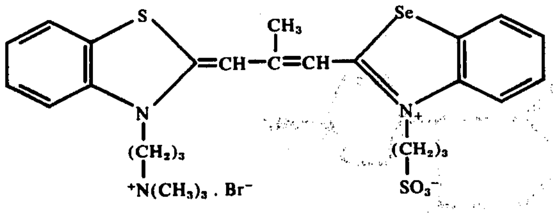
(K)
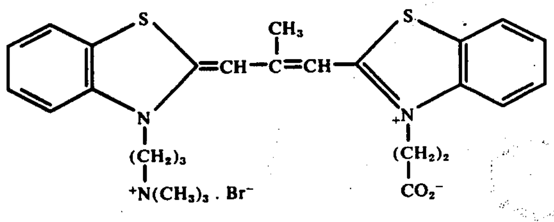
(L)
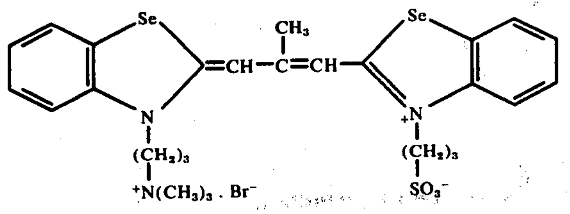
(M)
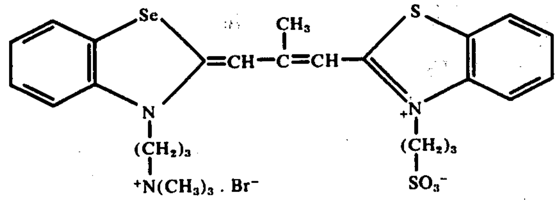
(N)
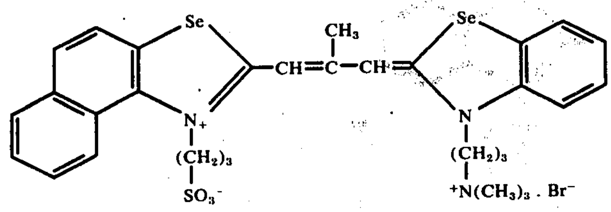
(O)
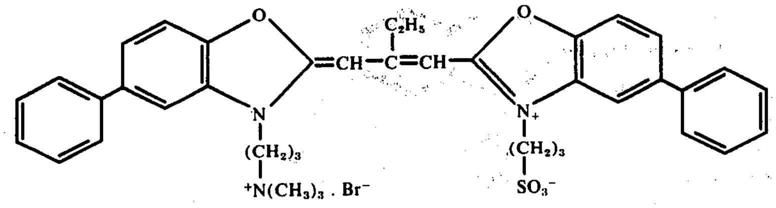
(P)
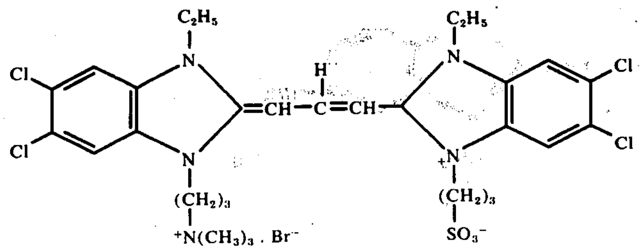

-continued
(Q)
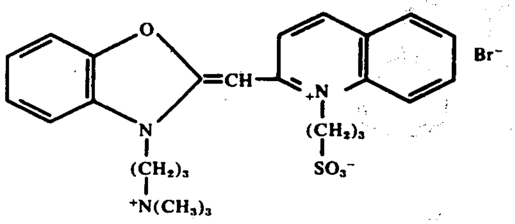
(R)
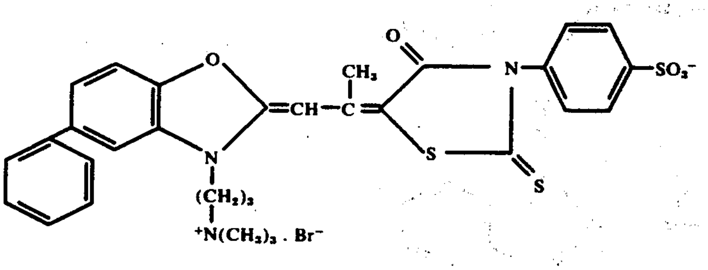
(S)
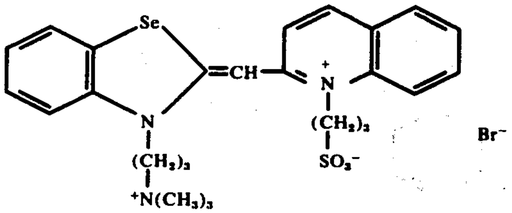
(T)
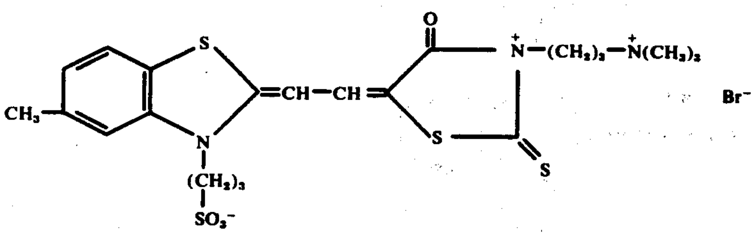
(U)
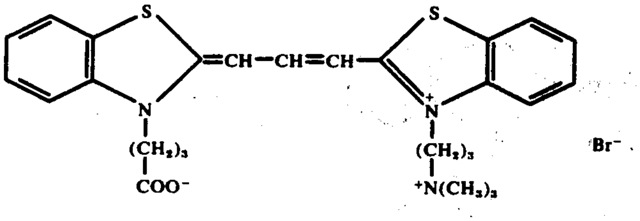
(V)
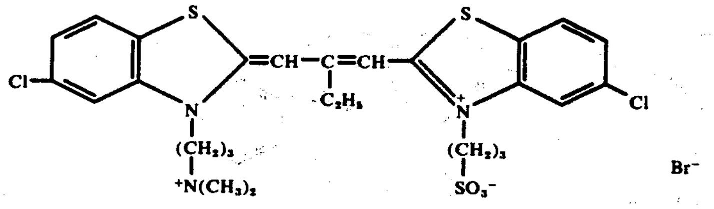
(W)
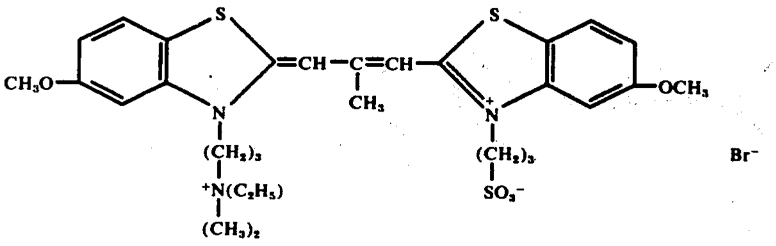

-continued (X)

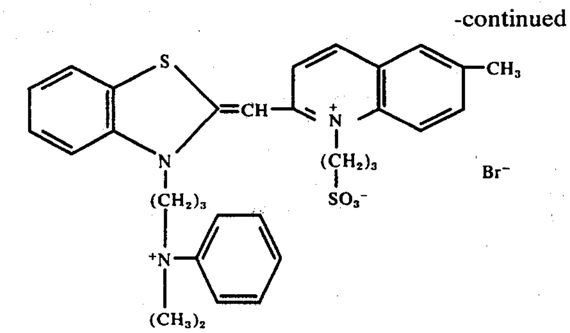

(Y)

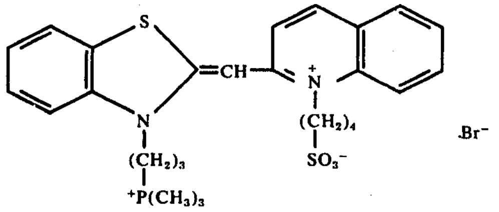

(Z)

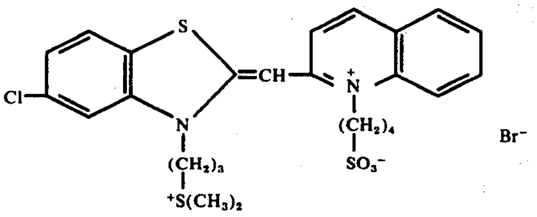

The cyanine dyes of the present invention may be prepared by condensing a compound of the formula:

IV

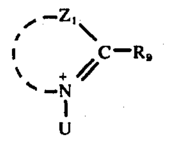

wherein $R_9$ is an alkyl group, preferably comprising from 1 to 3 carbon atoms and U is a $—R—X^+$ or $—R—Y^-$ group in the presence of a base with a compound of the formula:

V

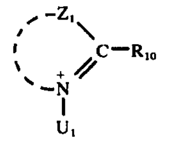

wherein $R_{10}$ is a halo, alkylmercapto or arylmercapto group and $U_1$ is $—R—Y^-$ when U is $—R—X^+$ and U is $—R—Y^-$ when $U_1$ is $—R—X^+$, to provide cyanine dyes of Formula I wherein *m* is 1 and each Z is the same or different;

condensing in the absence of a base a first quaternary salt of Formula IV with an amidine such as N,N-diphenylformamidine or in the presence of a base with the anhydride of a carboxylic acid, converting the product thereof to the thio analogue, alkylating the thio radical and condensing the resultant product with a second quaternary salt of Formula IV in the presence of a base wherein $U_1$ is $—R—X^+$ when U of the first quaternary salt is $—R—Y^-$ and $—R—Y^-$ when U of the first quaternary salt is $—R—X^+$, to provide cyanine dyes of Formula I wherein *m* is 2 and each Z is the same or different; and condensing in the absence of base a first quaternary salt of Formula IV with a β-arylaminoacrolein anil salt and directly condensing the product thereof in the presence of a base with a second quaternary salt of Formula IV as set forth immediately above to provide a cyanine dye of Formula I wherein *m* and each Z is the same or different.

The aforementioned base comprises a basic condensing agent such as an organic amine, for example, tri-n-propylamine, tri-n-butylamine, triisoamylamine, triethylamine, trimethylamine, dimethylaniline, diethylaniline, pyridine, n-alkyl-piperidine, etc., and most preferably an organic tertiary amine having a dissociation constant greater than pyridine ($1 \times 10^{-5}$); an alkali metal carboxylate in a carboxylic anhydride, for example, sodium acetate in acetic anhydride; etc.; or an alkali metal hydroxide, for example, sodium hydroxide, potassium hydroxide, etc. Preferably, the stated condensation reaction takes place in the presence of heat and in a substantially inert reaction medium such as lower molecular weight alcohol, for example, ethyl, n-propyl, isopropyl, n-butyl or isobutyl alcohol or methoxy ethanol; tricresylphosphate; or a phenol; or a reaction medium itself comprising the condensing agent such as pyridine.

As examples of the aforementioned carboxylic acid anhydrides, mention may be made of acetic anhydride, propionic anhydride, etc.

The quaternary salts of Formula IV may be readily prepared by condensing a compound of the formula:

VI

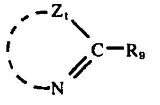

with a halogenated sulfonic acid, carboxylic acid, or a sultone such as 2-bromoethane sulfonic acid, 3-bromopropionic acid, bromoacetic acid, 4-bromobutyric acid, propane sultone, butane sultone, etc. to provide quaternary salts of Formula IV wherein U or $U_1$ is $-R-Y^-$ and with Halogen$-R-X^+$ $W^-$ wherein U or $U_1$ is $-R-X^+$.

One method by which the merocyanine dyes of Formula I may be prepared is by condensing in the presence of a quaternary salt of Formula IV with a compound of the formula:

VII

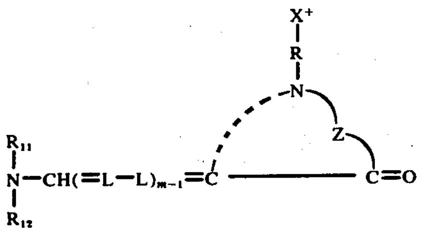

wherein $R_{11}$ represents hydrogen or an acyl group of a carboxylic acid such as, for example, acetyl, propionyl or benzoyl and $R_{12}$ represents an aryl group having 6 or 12 nuclear carbon atoms such as phenyl, diphenyl, xylyl, or naphthyl; or condensing in the presence of base a quaternary salt of the formula:

VIII

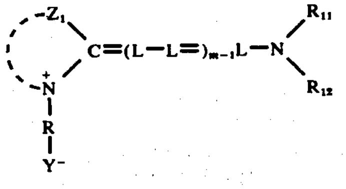

with a quaternary salt of the formula:

IX

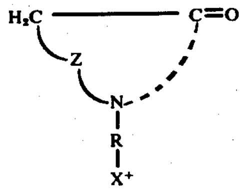

As examples of the specific synthesis of cyanine dyes of the class set forth in Formula I, for the purpose of illustration solely and not intended to be limiting in any manner, the cyanine dye of Formula (A) may be prepared by dissolving 1.6 grams of (1)

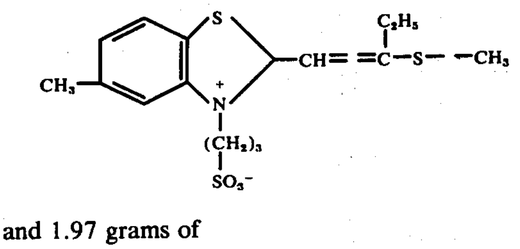

and 1.97 grams of (2)

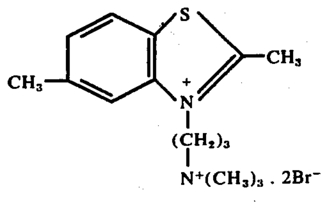

in 200 cc. of isopropanol; adding 2 cc. of triethylamine; stirring at 110° C. for 1 hour; cooling the mixture to room temperature; adding 100 cc. of acetone to the mixture; and cooling the mixture in a refrigerator overnight. The resultant crystalline product is removed by filtration and extracted with isopropanol for 16 hours to provide 1.5 grams of the cyanine dye of Formula (A); $\lambda_{max.}$ (in $CH_3OH$) = 567 M$\mu$.

| Elemental Analysis: | % C | % H | % N | % S |
|---|---|---|---|---|
| Calculated: | 51.94 | 6.25 | 5.52 | 13.87 |
| Found: | 51.74 | 6.11 | 5.67 | 13.92 |

The cyanine dye of Formula (F) may be prepared by dissolving 0.86 grams of (3)

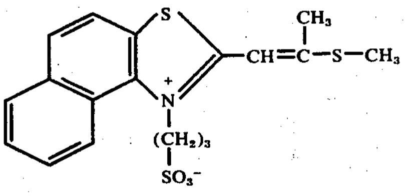

and 1.0 grams of the quaternary salt of Formula (2) in 15 cc. of phenol; adding 1 cc. of triethylamine; stirring for 1 hour at 110° C.; cooling the mixture to room temperature; adding 50 cc. of acetone, and stirring at room temperature for 16 hours. The resultant crystalline product is removed by filtration, extracted wth isopropanol for 16 hours, and vacuum dried to provide 0.5 grams of the cyanine dye of Formula (F); $\lambda_{max.}$ (in $CH_3OH$) = 575 M$\mu$.

The cyanine dye of Formula (G) may be prepared by dissolving 1.0 grams of the quaternary salt of Formula (3) and 1.23 grams (4)

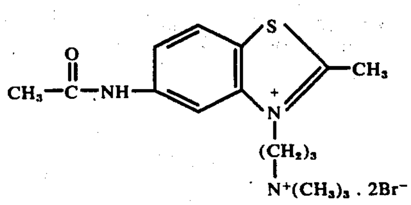

in 10 cc. of phenol; adding 1 cc. of triethylamine; stirring at 110° C. for 2 hours; cooling the mixture to room temperature; and adding acetone. The resultant crystalline product is removed by filtration, dissolved in methanol, and ether added to provide a 53% yield of the cyanine dye of Formula (G); $\lambda_{max.}$ (in $CH_3OH$) = 587 M$\mu$.

| Elemental Analysis: | % C | % H | % O |
|---|---|---|---|
| Calculated: | 54.15 | 5.37 | 8.75 |
| Found: | 54.18 | 5.52 | 8.93 |

The cyanine dye of Formula (C) may be prepared by dissolving 1.0 grams of (5)

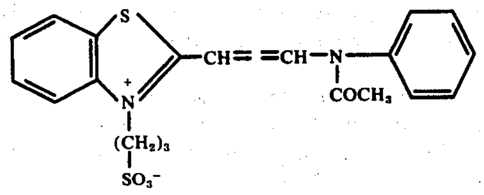

and 0.6 grams of (6)

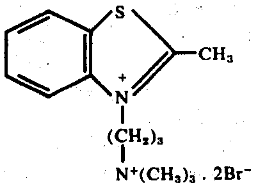

in 10 cc. of phenol, adding 1 cc. of triethylamine, stirring at 110° C. for 2 hours, adding acetone and letting the mixture stand. The resultant crystalline product is removed by filtration and extracted with isopropanol for 72 hours to provide a 68% yield of the cyanine dye of Formula (C); $\lambda_{max.}$ (in $CH_3OH$) = 565 $M\mu$.

The cyanine dye of Formula (B) may be prepared by dissolving 0.6 grams of the quaternary salt of Formula (1) and 0.7 grams of (7)

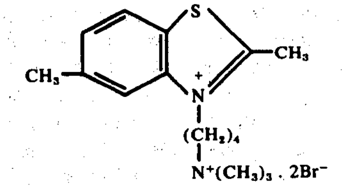

in 20 cc. of isopropanol at reflux temperature, adding 0.5 cc. of triethylamine, stirring at reflux temperature for 15 minutes. On cooling, the resultant crystalline product is removed by filtration, washed with isopropanol and vacuum dried to provide 0.6 grams of the cyanine dye of Formula (B); $\lambda_{max.}$ (in $CH_3OH$) = 567 $M\mu$.

| Elemental Analysis: | % C | % H | % N | % S | % Br |
|---|---|---|---|---|---|
| Calculated: | 54.69 | 6.22 | 6.17 | 14.13 | 11.74 |
| Found: | 54.50 | 5.93 | 5.85 | 13.85 | 11.50 |

The cyanine dye of Formula (E) may be prepared by dissolving 1.1 grams of (8)

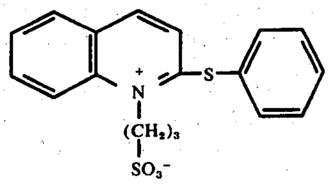

and 1.3 grams of the quaternary salt of Formula (6) in 5 cc. of pyridine at 100° C. 0.3 grams of triethylamine is added and the solution heated at 110° C. for about 2.5 hours. The cooled product mixture is poured into 350 cc. of a 5:1 acetone/ether mixture. 1.7 grams of crystalline cyanine dye of Formula (E) separated from the mixture and was purified by Soxhlet extraction with acetone for about 2 hours and vacuum dried at 110° C. for 1 hour.

| Elemental Analysis: | % C | % H | % N | % S | % Br |
|---|---|---|---|---|---|
| Calculated: | 53.98 | 5.58 | 7.26 | 11.08 | 13.18 |
| Found: | 54.07 | 5.56 | 7.20 | 11.26 | 12.60 |
| Melting Point = 300° C. | | | | | |

As examples of the preparation of illustrative quaternary salts of the class set forth above in Formulae (1) to (8), the quaternary salt of Formula (6) may be prepared by adding 60.3 grams of $Br(CH_2)_3Br$ to precooled 30 cc. of $(CH_3)_3N$ in a 250 cc. steel bomb, sealing the bomb, raising the temperature of the bomb to room temperature and allowing to stand for 72 hours. The solid product 77 grams of $Br(CH_2)_3N^+(CH_3)_3\ Br^-$
(9)

is triturated and washed with ether until free of reactants and dried in vacuo over Drierite at 60° C.

A mixture of 22.0 grams of (10)

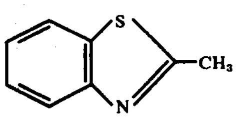

and 40.0 grams of the reactant of formula (9) is heated at 140° C. with vigorous stirring for 18 hours. The solid product broken up in ether and the resultant product is recrystallized from a 1:3 $C_2H_5OH/CH_3OH$ mixture, to provide 29.0 grams of the quaternary salt of Formula (6) M.P. = 155°–156° C.

The quaternary salt of Formula (1) may be prepared by heating a well-stirred mixture of 10.0 grams of (11)

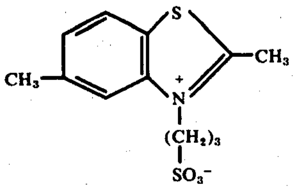

and 45 cc. of propionic anhydride at about 120° C. for 10 minutes. 15 cc. of triethylamine is added over a period of 5 minutes followed by heating at 120° C. for 45 minutes. The mixture is cooled and triturated in 300 cc. of ethyl ether to provide 13.0 grams of the product (12)

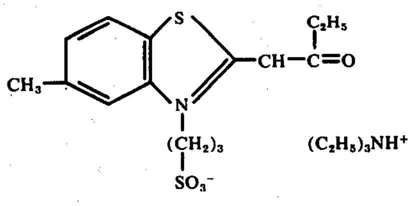

which is dissolved in 80 cc. of methanol, treated with 2 cc. of triethylamine, added to 200 cc. of ethyl ether, and chilled to yield 10.3 grams of product M.P. = 156°–158° C.

A well-stirred mixture of 4.15 grams of the compound of Formula (12) and 1.2 grams of $P_2S_5$ in 75 cc. of $CHCl_3$ is refluxed for 2 hours, cooled to room temperature, decanted. The solid is extracted with boiling $CHCl_3$, and the combined $CHCl_3$ extracts evaporated to dryness to provide 4.5 grams of the product

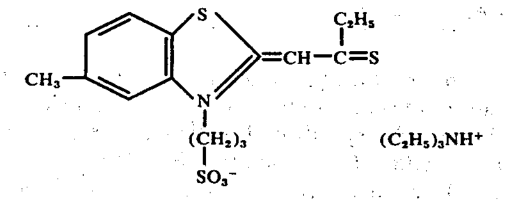
(13)

A well-stirred mixture of 4.5 grams of the compound of Formula (13) and 5 cc. of methyl iodide in 10 cc. of anhydrous methanol is allowed to stand at room temperature for 15 hours. The resultant precipitate is removed by filtration, washed with methanol and dried to yield 1.9 grams of the quaternary salt of Formula (3) M.P. = 267°–270° C.

The preferred silver halide dispersions employed for the fabrication of preferred photographic film unit-scomprising spectrally sensitized photoresponsive silver halide crystals, as specifically detailed immediately above, may be prepared by reacting a water-soluble silver salt, such as silver nitrate, with at least one water soluble halide, such as ammonium, potassium or sodium bromide, preferably together with a corresponding iodide, in an aqueous solution of a peptizing agent such as a colloidal gelatin solution; digesting the dispersion at an elevated temperture, to provide increased crystal growth; washing the resultant dispersion to remove undesirable reaction products and residual water-soluble salts by chilling the dispersion, noodling the set dispersion, and washing the noodles with cold water, or, alternatively, employing any of the various flocc systems, or procedures, adapted to effect removal of undesired components, for example, the procedures described in U.S. Pat. Nos. 2,614,928; 2,614,929; 2,728,662; and the like; after-ripening the dipersion at an elevated temperature in combination with the addition of gelatin and/or such other polymeric materials as may be desired and various adjuncts, for example, the previously detailed chemical sensitizing agents and the like; all according to the traditional procedures of the art, as described in Neblette, C. B., Photography Its Materials and Processes, sixth Ed., 1962.

Optical sensitization of the dispersion's silver halide crystals may then be accomplished by contact of the emulsion composition with an effective concentration of the selected cyanine optical sensitizing dye or dyes, each of which dyes has preferably been dissolved in an appropriate dispersing solvent such as methanol, ethanol, pyridine, acetone, water, and the like; all according to the traditional procedures set forth in the art such as, for example, the U.S. and foreign patents identified above. In general, the concentration of sensitizing dye or dyes may be varied empirically in accordance with the characteristics of the particular photoresponsive material such as the silver halide selected and the sensitizing effects desired which in the instance of preferred silver iodobromide dispersions will ordinarily fall within the range of about 0.05 to 5 grams per 100 grams of silver halide measured as silver.

Subsequent to spectral sensitization, any further desired additives, such as coating aids and the like, may be incorporated in the emulsion and the mixture coated and processed according to the conventional procedures known in the photographic emulsion manufacturing art.

Alternatively, an emulsion coating can be prepared and coated on a suitable support whereupon the coating may be sequentially immersed in the respective solutions of cyanine dyes.

Specifically, a gelatino silver iodobromide emulsion prepared as detailed above and comprising a gelatin/silver ratio of about 1:1 and about 4 mole percent bromide concentration may be chemically sensitized with gold and sulfur as, for examle, by the addition, at about 56° C., PH 5 and pAg 9, of a optimally sensitizing amount of a solution comprising 0.1 gram of ammonium thiocyanate in 9.9 cc. of water and 1.2 cc. of a solution containing 0.097 grams of gold chloride in 9.9 cc. of water, and a 0.02% aqueous sodium thiosulfate solution.

The formulation may be optically sensitized in accordance with the present invention by the addition of a sensitizing concentration of one or more of the cyanine optical sensitizing dyes detailed above as, for example, 1,2 and 4 mgs. per gram of silver of the cyanine dye of Formula (A) dissolved in methanol.

The optically sensitized formulation may then be coated on an appropriate support as, for example, cellulose triacetate film base and the film units thus prepared exposed in a conventional wedge spectrograph.

Upon processing with a photographic developing composition as, for exmple, a conventional processing composition of the type commercially distributed by Eastman Kodak Company, Rochester, N.Y., U.S.A., under the trade name of "Dektol Developer" and comprising an aqueous alkaline solution of monomethyl-para-amino phenol sulfate and hydroquinone, and a conventional acid stop bath, the resultant spectrograms will detail the sensitivity characteristics of the optically sensitized formulation which may be directly compared with a nonoptically sensitized film unit or film units optically sensitized with selected prior art dyes.

It has been specifically found that in general preferred mesoalkyl (methyl, ethyl, etc.) substituted carbocyanine dyes of the present invention unexpectedly exhibit considerably higher extinction coefficients, e.g., in the range of about 150,000 to 200,000 than the corresponding 3,3'-dialkyl, quaternary ammonium, sulfo or carboxy substituted carbocyanine dyes of the prior art and that the preferred dyes exhibit a bathochromic spectal absorption shift in the $\lambda_{max.}$ of about 15 Mμ in solution. In addition, the dyes of the present invention have been further found to possess increased solubility in water as compared with corresponding prior art materials and thus there is facilitated direct disposition of the such dyes in photoresponsive compositions with concomitant decreased employment of, if not the absence of, photographically deleterious organic solvent adjuvants such as methanol and the like traditionally employed to effect disposition of cyanine optical sensitizing dyes.

As previously detailed, the photoresponsive crystals of the present invention may be employed as the photosensitive component of a photographic emulsion by incorporation within a suitable binder and the coating and processing of the thus prepared emulsion according to conventional procedures known in the photographic manufacturing art.

The photoresponsive crystal material of the photographic emulsion will, as previously described, preferably comprise a crystal of a siler compound, for example, one or more of the silver halides such as silver chloride, silver iodide, silver bromide, or mixed silver halides such as silver chlorobromide, silver iodobromide or silver iodochlorobromide of varying halide ratios and varying silver concentrations. The formulated photographic emulsions may be used for the preparation of orthochromatic, panchromatic and infrared sensitive photographic films.

The fabricated emulsion may be coated onto various types of rigid or flexible supports, for example, glass, paper, metal, polymeric films of both the synthetic types and those derived from naturally occurring products, etc. Especially suitable materials include paper; aluminum; polymethacrylic acid, methyl and ethyl esters; vinyl chloride polymers; polyvinyl acetals; polyamides such as nylon; polyesters such as the polymeric films derived from ethylene glycol terephthalic acid; polymeric cellulose derivatives such as cellulose acetate, triacetate, nitrate, propionate, butyrate, acetate-butyrate, or acetate-propionate; polycarbonates; polystyrenes, etc.

The emulsions may include the various adjuncts, or addenda, according to the techniques disclosed in the art, such as speed increasing compounds of the quaternary ammonium type, as described in U.S. Pat. Nos. 2,271,623; 2,288,226; and 2,334,864; or of the polyethyleneglycol type, as described in U.S. Pat. No. 2,708,162, or of the preceding combination, as described in U.S. Pat. No. 2,886,437; or the thiopolymers, as described in U.S. Pat. Nos. 3,046,129 and 3,046,134.

The emulsions may also be stabilized with the salts of the noble metals such as ruthenium, rhodium, palladium, iridium and platinum, as described in U.S. Pat. Nos. 2,566,245 and 2,566,263; the mercury compounds of U.S. Pat. Nos. 2,728,663; 2,728,664 and 2,728,665; triazoles of U.S. Pat. No. 2,444,608; the azaindines of U.S. Pat. Nos. 2,444,605; 2,444,606; 2,444,607; 2,450,297; 2,444,609; 2,713,541; 2,743,181; 2,716,062; 2,735,769; 2,756,147; 2,772,164; and those disclosed by Burr in "Wiss. Phot.", volume 47, 1952, pages 2–28; the disulfides of Belgian Pat. No. 569,317; the benzothiazolium compounds of U.S. Pat. Nos. 2,131,038 and 2,694,716; the zinc and cadmium salts of U.S. Pat. No. 2,839,405; and the mercapto compounds of U. S. Pat. No. 2,819,965.

Hardening agents such as inorganic agents providing polyvalent metalic atoms, specifically polyvalent aluminum or chromium ions, for example, potash alum $[K_2Al_2(SO_4)_4.24H_2O]$ and chrome alum $[K_2CR_2(SO_4)_4.24H_2O]$ and inorganic agents of the aldehyde type, such as formaldehyde, glyoxal, mucochloric acid, etc.; the detone type such as diacetyl; the quinone type; and the specific agents descrbied in U.S. Pat. Nos. 2,080,019; 2,725,294; 2,725,295; 2,725,305; 2,726,162; 2,732,316; 2,950,197; and 2,870,013, may be incorporated in the emulsion.

The emulsion may also contain one or more coating aids such as saponin; a polyethyleneglycol of U.S. Pat. No. 2,831,766; a polyethyleneglycol ether of U.S. Pat. No. 2,719,087; a taurine of U.S. Pat. No. 2,739,891; a maleopimarate of U.S. Pat. No. 2,823,123; an amino acid of U.S. Pat. No. 3,038,804; a sulfosuccinamate of U.S. Pat. No. 2,992,108; or a polyether of U.S. Pat. No. 2,600,831; or a gelatin plasticizer such as glycerin; a dihydroxyalkane of U.S. Pat. No. 2,960,404; a bis-glycolic acid ester of U.S. Pat. No. 2,904,434; a succinate of U.S. Pat. No. 2,940,854; or a polymeric hydrosol of U.S. Pat. No. 2,852,386.

As the binder for photosensitive crystals, the aforementioned gelatin may be, in whole or in part, replaced with some other colloidal material such as albumin, casein; or zein; or resins such as cellulose derivatives an vinyl polymers such as described in an extensive multiplicity of readily available U.S. and foreign patents.

The photographic emulsions may be employed in black-and-white or color photographic systems, of both the additive and subtractive types, for example, those described in *Photography, Its Materials and Processes*, supra. The photoresponsive crystals may also be employed in the fabrication of photographic emulsions which form latent images predominantly on the surface of the crystal or in emulsions which form latent images predominantly inside the crystal such as those described in U.S. Pat. No. 2,592,250.

The fabricated emulsions may also be employed in silver diffusion transfer processes of the types set forth in U.S. Pat. Nos. 2,352,014; 2,500,421; 2,543,181; 2,563,342; 2,565,376; 2,584,029; 2,584,030; 2,603,565; 2,616,807; 2,635,048; 2,644,756 2,647,055; 2,662,822; 2,698,236; 2,698,237; 2,698,238; 2,698,245; 2,702,244; 2,704,721; 2,740,715; 2,759,825; 2,774,667; 2,823,122; 2,923,623; 2,938,792; 2,962,377; 2,984,565; 3,003,875; 3,043,690; 3,087,815; 3,087,816; 3,091,530; 3,108,001 and 3,113,866; in additive color diffusion transfer processes of the types disclosed in U.S. Pat. Nos. 2,614,926; 2,726,154; 2,944,894; 2,992,103 and 3,087,815; and in subtractive color diffusion transfer processes of the types disclosed in U.S. Pat. Nos. 2,559,643; 2,600,996; 2,614,925; 2,647,049; 2,661,293; 2,698,244; 2,698,798; 2,774,668; 2,802,735; 2,855,299; 2,892,710; 2,909,430; 2,968,554; 2,983,605; 2,983,606; 2,992,104; 2,992,105; 2,992,106; 2,997,390; 3,003,872; 3,015,501; 3,019,104; 3,019,124; 3,022,166; 3,022,167; 3,039,869; 3,043,689; 3,043,692; 3,444,873; 3,047,386; 3,065,074; 3,069,262; 3,069,264; 3,076,808; 3,076,820; 3,077,400; 3,077,402; 3,415,644; 3,415,645; 3,415,646; 3,473,925; 3,573,042; 3,573,043; 3,573,044; 3,576,625 and 3,576,626; etc.

The photoresponsive crystals of the present invention may also be employed as the photosensitive component of information recording elements which employ the distribution of a dispersion of relatively discrete photoresponsive crystal, substantially free from interstitial binding agents, on a supporting member such as those previously designated, to provide image recording elements, for example, as described in U.S. Pat. Nos. 2,945,771; 3,142,566; 3,142,567; Newman, *Comment on Non-Gelatin Film*, B.J.O.P., 534, Sept. 15, 1961; and Belgian Pat. Nos. 642,557 and 642,558.

As taught in the art, the concentration of silver halide crystals forming a photographic emulsion and the relative structural parameters of the emulsion layer, for example, the relative thickness, and the like, may be varied extensively and drastically, depending upon the specific photographic system desired and the ultimate employment of the selective photographic system.

In conventional photographic processes, for the formation of silver images, a latent image is provided by selective exposure of a photosensitive photographic emulsion, generally containing the aforementioned photoresponsive silver halide crystals or the like. The thus-produced latent image is developed, to provide a visible silver image, by a suitable contact with any of the photographic developing solutions set forth in the art. For the purpose of enhancing the resultant visible image's stability, the image may be suitably fixed, according to the procedures also well known to those skilled in the art. The resultant image-containing element may be then directly employed or, optionally, may be employed, where applicable, as a negative image, for example, to provide a reversed or positive image by conventional contact or projection printing processes employing suitable photosensitive printing papers.

In the conventional photographic subtractive color processes which find commercial utilization, color coupling techniques are generally employed to provide the requisite number of registered color images necessary for monochromatic and multichromatic reproduction. According to these techniques, one or more selectively photoresponsive, generally gelatinous, silver halide strata are selectively exposed to provide latent image record formation corresponding to the chromaticity of the selected subject matter. The resultant latent images are suitably developed by selective intimate contact between one or more color developing agents and one or more color formers or couplers to provide the requisite negative color images. Alternatively, the latent images are developed to provide visible silver images; the resultant visible images removed; the remaining residual silver halide exposed, and the second-formed exposure records developed by selective contact between one or more color developing agents and one or more color formers or couplers, in the presence of exposed silver halide to provide the desired colored positive image.

In diffusion transfer processes, for the formation of positive silver images, a latent image contained in an exposed, photosensitive, generally gelatinous, silver haide emulsion is developed and, substantially contemporaneous with development, a soluble silver complex is obtained by reaction of a silver halide solvent with the unexposed and undeveloped silver halide of the emulsion. The resultant soluble silver complex is, at least in part, transported in the directin of a suitable print-receiving element, and the silver of the complex precipitated in such element to provide the requisite positive image definition.

Additive color reproduction may be produced by exposing a photosensitive silver halide emulsion through an additive solor screen having filter media or screen elements, each of an individual additive color such as red, blue or green, and by viewing the resultant image, subsequent to development, through the same or a similar screen element. Alternatively, the photosensitive element may be employed to provide a silver transfer image analogous to the preceding description of diffusion transfer processing and the resultant transfer image may be viewed through the same, or a similar, additive color screen which is suitably registered with the silver transfer image carried by the print-receiving image.

Subtractive color reproduction may be provided by diffusion transfer techniques wherein one or more photo-responsive spectrally selective silver halide elements, having an appropriate subtractive color-providing material associated therewith, are selectively exposed to provide the requisite latent image record formations corresponding to the chromaticity of the selected subject matter and wherein the distribution of color-providing materials, by diffusion, to a suitable image-receiving element, is controlled, imagewise, as a function of the respective latent image record formations.

The photoresponsive crystals of the present invention may also be employed as the photoconductive component of electrophotographic materials, for example, inorganic photoconductive crystals such as zinc oxide, selenium, cadmium sulfide, cadmium telluride, indium oxide, antimony trisulfide, and the like, and organic photoconductive crystals such as anthracene, sulfur, benzidine, the aromatic furances of U.S. Pat. No. 3,140,946, and the like, as described in U.S. Pat. Nos. 2,987,395; 3,047,384; 3,052,540; 3.069,365; 3,110,591; 3,121,008; 3,125,447; and 3,128,179.

In preparing photoconductive layers, it is the usual practice to suspend the photoconductive crystal in a suitable solvent in the presence of an electrically insulating binder and then to dissolve the optical sensitizing dye in this composition prior to coating on a conducting support. Where the layers are thus prepared, the optical sensitizing components are added to the coating composition, prior to coating, in the manner of the instant invention as described hereinbefore.

Alternatively, an unsensitized photoconductive layer can be prepared and the coating then sensitized according to the previously described alternate procedure.

Preferred binders for use in preparing the photoconductive layers comprise polymers having fairly high dielectric strength and which are good electrically insulating film-forming vehicles. Materials of this type comprise styrene-butadiene copolymers; silicone resins; styrene-alkyd resins; soya-alkyd resins; poly(vinyl chloride); poly(vinylidene chloride); vinylidene chloride, acrylonitrile copolymers; poly(vinyl acetate); vinyl acetate, vinyl chloride copolymers; poly(vinyl acetals), such as poly(vinyl butyral); polyacrylic and methacrylic esters, such as poly(methyl methacrylate), poly(n-butyl methacrylate, poly(isobutyl methacrylate), etc.; polystyrene; nitrated polystyrene; polymethylstyrene; isobutylene polymers; polyesters, such as poly-(ethylene-alkaryloxy-alkylene terephthalate); phenol-formaldehyde resins; ketone resins; polyamides; polycarbonates, etc. Methods of making resins of this type have been described in the prior art, for example, styrene-alkyd resins can be prepared according to the method described in U.S. Pat. Nos. 2,361,019 and 2,258,423. Other types of binders which can be used in the photoconductive layers include such materials as paraffin, mineral waxes, and the like.

Solvents of choice for preparing the last-mentioned coating compositions can include a number of solvents such as benzene, toluene, acetone, 2-butanone, chlorinated hydrocarbons, e.g., methylene chloride, ethylene chloride, etc., ethers, e.g., tetrahydrofuran, or mixtures of these solvents, etc.

The photoconductive layers can then be coated on a conducting support in any well-known manner such as the conventional doctor-blade coating, swirling, dip-coating, and the like, techniques. Although photoconductive layers in some cases do not require a binder, it is usually beneficial to include some binder in a coating composition of this type, for example, as little as 1 weight percent.

In preparing the coating composition, useful results will be obtained where the photoconductor substance is present in an amount equal to at least about 1 weight percent of the coating composition. The upper limit in the amount of photoconductor substance present is not critical. As indicated previously, the polymeric materials in many cases do not require a binder in order to obtain a self-supporting coating on the support. In those cases where a binder is employed, it is normally desired that the photoconductive substance be present in an amount from about 1 weight percent of the coating composition to about 99 weight percent of the coating composition. A preferred weight range for the photoconductor substance in the coating composition is from 10 weight percent to about 60 weight percent.

Coating thicknesses of the photoconductive composition on a support can vary widely. Normally a wet coating in the range from about 0.001 inch to about 0.01 inch is useful. A preferred range of wet coating thickness may be found to be in the range from about 0.002 inch to about 0.006 inch.

Suitable supporting materials for the photoconductive layers of the present invention can include any of the electrically conducting supports, for example, paper (at a relative humidity above 20 percent); aluminum-paper laminates; metal foils, such as aluminum foil, zinc foil, etc.; metal plates, such as aluminum, copper, zinc, brass, and galvanized plates, regenerated cellulose and cellulose derivatives; certain polyesters and especially those having a thin electroconductive layer (e.g., cuprous iodide) coated thereon; and the like.

The photoconductive elements can be employed in any of the well-known electrophotographic processes which require photoconductive layers. One such process is the xerographic process. In a process of this type, the electrophotographic element is given a blanket electrostatic charge by placing the same under a corona discharge which serves to give a uniform charge to the surface of the photoconductive layer. This charge is retained by the layer owing to the substantial insulating property of the layer, i.e., the low conductivity of the layer in the dark. The electrostatic charge formed on the surface of the photoconducting layer is then selectively dissipated from the surface of the layer by exposure to light through a negative by a conventional exposure operation such as, for example, by a contact-printing technique, or by lens projection of an image, etc., to form a latent image in the photoconductive layer. By exposure of the surface in this manner, a charged pattern is created by virture of the fact that light causes the charge to leak away in proportion to the intensity of the illumination in a particular area. The charge pattern remaining after exposure is then developed, i.e., rendered visible, by treatment with a medium comprising electrostatically attractable particles having optical density. The developing electrostatically attractable particles can be in the form of a dust, i.e., powder, a pigment in a resinous carrier, i.e., toner, or a liquid developer may be used in which the developing particles are carried in an electrically insulating liquid carrier. Methods of development of this type are widely known and have been described in the patent literature in such patents, for example, as U.S. Pat. No. 2,296,691, and the like. In process of electrophotographic reproduction such as in xerography, by selecting a developing particle which has one of its components, a low-melting resin, it is possible to treat the developed photoconductive material with heat and cause the powder to adhere permanently to the surface of the photoconductive layer. In other cases, a transfer of the image formed on the photoconductive layer can be made to a second support which would then become the final print. Techniques of the type indicated are well known in the art and have been described in U.S. Pat. Nos. 2,297,691 and 2,551,582 and in "RCA Review", Vol. 15 (1954), pages 469–484.

Since certain changes may be made in the above product and process without departing from the scope of the invention herein involved, it is intended that all matter contained in the above description or shown in the accompanying drawings shall be interpreted as illustrative and not in a limiting sense.

What is claimed is:

1. A cyanine dye of the formula:

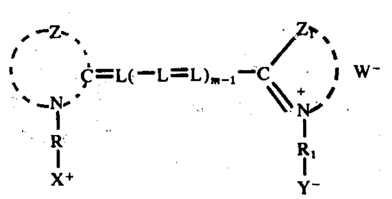

wherein L represents a methine group; $m$ represents a positive integer of from 1 to 3, inclusive; Z and $Z_1$ each represents the nonmetallic atoms necessary to complete a heterocyclic ring system of the azole or azine series; R and $R_1$ each represents a divalent aliphatic group, cycloalkylene group or arylene group; $X^+$ represents a quaternary ammonium, sulfonium or phosphonium group; $Y^-$ represents a $—SO_3^-$ or a $—COO^-$ group; and $W^-$ represents an acid anion.

2. A cyanine dye as defined in claim 1 of the formula:

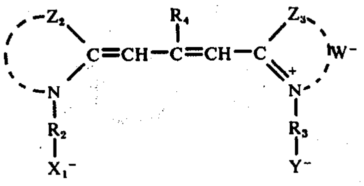

wherein $Z_2$ and $Z_3$ each represents the nonmetallic atoms necessary to complete a heterocyclic ring system of the thiazole, selenazole, oxazole, imidazole or pyridine series; $R_2$ and $R_3$ each represents a divalent aliphatic group comprising from 1 to 5 carbon atoms; $R_4$ represents an alkyl group comprising 1 to 5 carbon atoms, or an aromataic group comprising 6 nuclear carbon atoms; and $X_1^+$ represents a $—N^+ (R_5)_3$ group wherein each $R_5$ represents an alkyl group comprising from 1 to 4 carbon atoms.

3. A cyanine dye as defined in claim 1 of the formula:

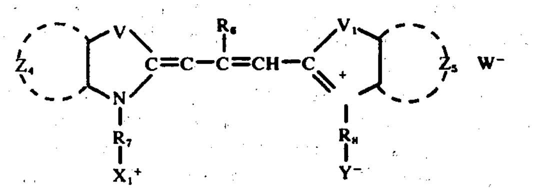

wherein V and $V_1$ each represents oxygen, selenium, sulfur or

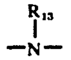

wherein $R_{13}$ represents an alkyl group comprising from 1 to 5 carbon atoms; $Z_4$ and $Z_5$ each comprises the nonmetallic atoms necessary to complete an annulated benzene or naphthalene ring; $R_6$ represents a hydrogen, methyl, or ethyl group; and $R_7$ and $R_8$ each represents an alkylene group comprising from 1 to 5 carbon atoms; and $X_1^+$ represents a $—N^+(R_5)_3$ group wherein each $R_5$ represents an alkyl group comprising from 1 to 4 carbon atoms.

4. A cyanine dye as defined in claim 3 of the formula:

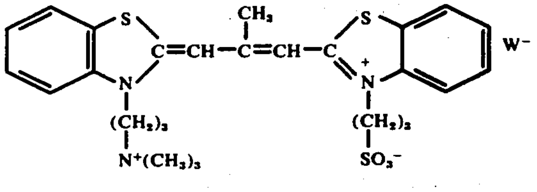

5. A cyanine dye as defined in claim 3 of the formula:

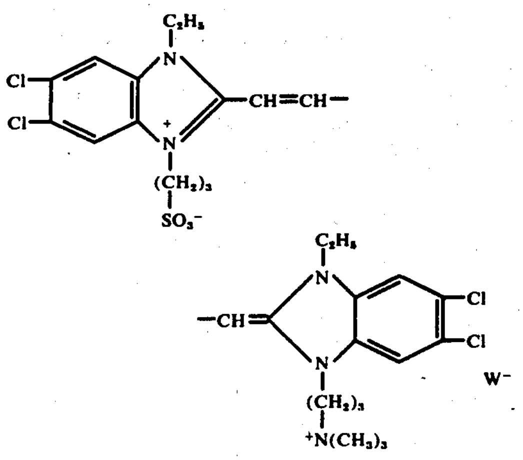

6. A cyanine dye as defined in claim 3 of the formula:

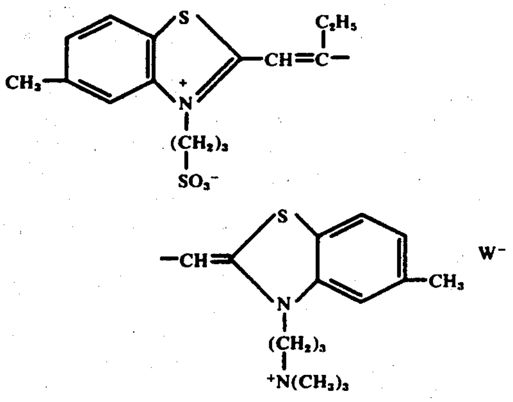

7. A cyanine dye as defined in claim 3 of the formula:

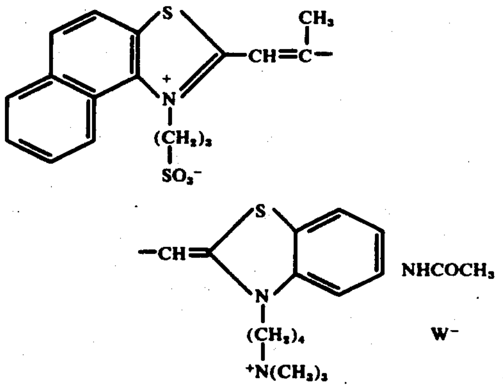

8. A cyanine dye as defined in claim 3 of the formula:

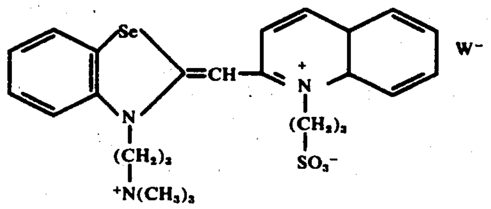

* * * * *